(12) United States Patent
Roy et al.

(10) Patent No.: US 8,577,106 B2
(45) Date of Patent: Nov. 5, 2013

(54) READY AUTOMATED SCREENING, DIAGNOSIS AND CLASSIFICATION TECHNIQUE FOR ALZHEIMER'S DISEASE USING MAGNETIC RESONANCE IMAGING SIGNAL FROM VENTRICULAR ZONE CONTOUR OF BRAIN

(75) Inventors: Prasun Roy, Gurgaon (IN); Subramanyam V. P. Rallabandi, Gurgaon (IN)

(73) Assignees: Department of Biotechnology, New Delhi (IN); National Brain Research Centre, Haryana (IN)

( * ) Notice: Subject to any disclaimer, the term of this patent is extended or adjusted under 35 U.S.C. 154(b) by 161 days.

(21) Appl. No.: 13/133,038

(22) PCT Filed: Feb. 10, 2009

(86) PCT No.: PCT/IN2009/000095
§ 371 (c)(1),
(2), (4) Date: Aug. 8, 2011

(87) PCT Pub. No.: WO2010/052731
PCT Pub. Date: May 14, 2010

(65) Prior Publication Data
US 2011/0286650 A1  Nov. 24, 2011

(30) Foreign Application Priority Data
Nov. 7, 2008 (IN) ............... 2532/DEL/08

(51) Int. Cl.
*G06K 9/00* (2006.01)

(52) U.S. Cl.
USPC ........................................ 382/128

(58) Field of Classification Search
USPC ............... 382/100, 128–134; 128/922–925; 250/455; 356/39–49; 600/407–414, 600/424–426; 345/581–618
See application file for complete search history.

(56) References Cited

U.S. PATENT DOCUMENTS

| | | | |
|---|---|---|---|
| 5,185,809 A | 2/1993 | Kennedy et al. | |
| 5,956,125 A | 9/1999 | Rosse et al. | |
| 6,067,986 A | 5/2000 | Kluger et al. | |
| 6,162,186 A | 12/2000 | Scinto et al. | |
| 6,264,625 B1 | 7/2001 | Rubenstein et al. | |
| 6,654,695 B2 | 11/2003 | Shimura et al. | |
| 7,070,945 B2 | 7/2006 | Jackowski et al. | |
| 7,074,576 B2 | 7/2006 | Jackowski et al. | |
| 2008/0298653 A1 | 12/2008 | Amunts et al. | |

FOREIGN PATENT DOCUMENTS

| | | |
|---|---|---|
| EP | 1739621 A1 | 1/2007 |
| WO | 2007065589 A1 | 6/2007 |

*Primary Examiner* — Atiba O Fitzpatrick
(74) *Attorney, Agent, or Firm* — The Webb Law Firm

(57) ABSTRACT

The invention relates to a fully automated screening, diagnosis and classification technique for Alzheimer's disease using magnetic resonance imaging signals from the ventricular zone contour of the brain to get a fundamental index of brain deterioration comprising the steps: —obtaining a gray scale MRI image of the brain region; —applying a contour edge-detecting algorithm to the image; —employing a grid covering method for calculating a first order metric index of ventricular zone contour; —superimposing metric square grids of increasing edge length to the binary contour image and counting the metric grid squares; —plotting the logs of metric grid squares against the logs of edge lengths, wherein the gradient of the plot is the linear topological metric index.

16 Claims, 2 Drawing Sheets

Figure 1:
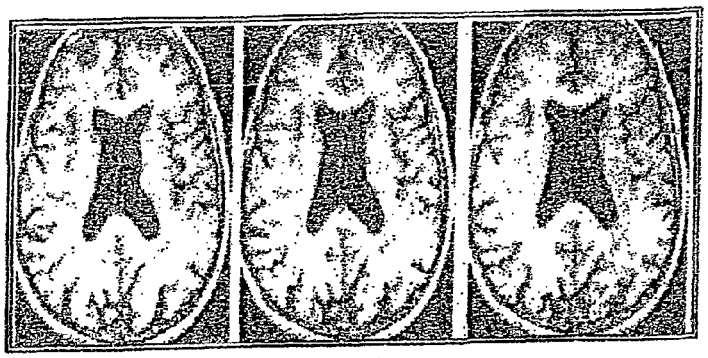

READY AUTOMATED SCREENING, DIAGNOSIS AND CLASSIFICATION TECHNIQUE FOR ALZHEIMER'S DISEASE USING MAGNETIC RESONANCE IMAGING SIGNAL FROM VENTRICULAR ZONE CONTOUR OF BRAIN

FIELD OF INVENTION

This invention relates to a ready automated screening, diagnosis & classification technique for Alzheimer's disease using magnetic resonance imaging signal from ventricular zone contour of brain.

BACKGROUND OF INVENTION

Well acknowledged nationally and internationally, the problem of early diagnosis of dementia, particularly Alzheimer's disease and Mild cognitive deficit, is a landmark problem in chronic diseases and public health worldwide. This burden is particularly becoming a demographic problem, not only in industrial nations, but also in developing countries like China, India and Brazil (where population above 50 year are increasing dramatically). Numerous studies by W.H.O, N.I.H, European Commission and World Bank have underscored the extreme need for an automated ready objective imaging test for diagnosing dementia, which can also be used by a technician (non-physician) in an epidemiological or community based screening perspective to monitor geriatric population with memory problem. The proposed invention exactly fits all these requirements. This invention will be of much interest and utility to the medical, neurological, psychiatric, radiological, psychotherapeutic and geriatric community, as well as to imaging scientists and engineers, epidemiologists, public health specialists or policy-makers, who need to tackle or plan for the ever-growing societal burden imposed by the rapidly increasing elderly population.

Most of the earlier pathological/biochemical techniques for Alzheimer diagnosis, use biopolymer markers, peptide markers, or markers for amyloid deposits and tau proteins. These procedures are invasive, and need brain tissue materials from the patient, and are, hence, not commonly feasible. On the other hand, there are morphometric or volumetric imaging techniques to correlate with dementia, but there procedures need long time-consuming manual intervention by neuroradiologists (not usually obtainable), and suffer from human visual subjective errors, the accuracy being around 75-90%. Furthermore, other exploratory neuroimaging procedures that use automated image processing approach to diagnose Alzheimer's disease, have an accuracy up to 85-89%, and rely on imaging every voxel of brain, with heavy computational processing (using a space of about 100,000 dimensions), whilst needing repeated manual checking of misregistration and image thresholding. All these said techniques have utilized patient data sets below 100 individuals, whereas the development of inventor's technique has involved much more individuals, around 200 subjects.

The quantitative procedure and computational algorithms for the classification of the neurodegenerative brain image based on $T_1$-weighted MR scan has been developed and the procedure has been validated using tested clinical patient datasets (over a large population of over 200 individuals), and the procedure is applicable to MRI scanners of all the Electronics Engineering Manufacturers in the world who make these equipments, such as Siemens (Germany), General Electric (USA), Philips (The Netherlands), Picker (UK), LG Electronics (Korea), Toshiba (Japan) etc. Our testing has been done on two different datasets of dementia and Alzheimer's disease at different centers and of scanners of different manufactures. At first, we initially explored the feasibility of the initial image standardization methodology by using image from various medical centers in India, across the four zones of the country, namely North (Delhi), South (Bangalore), East (Calcutta) and West (Bombay).

Thereafter, inventors evolved the technology by using and testing the various clinical imaging scan datasets taken under standard protocols [such as OASIS platform of National Institute of Health (NIH), and LONI platform of Alzheimer's Disease Neuroimaging Initiative (ADNI). The validation of the proposed approach has been done on randomly selected ⅔ of patients as training sets and ⅓ of patients as unseen testing sets. This was repeated three times, by further randomized selection. For each training set, we built a classification algorithm based on specific topological indices, thence we imparted a performance trial of the algorithm by using them on the unseen test set. Inventors found that the same algorithm performed satisfactory classification on all the instances. Our technique is user friendly and automated, does not need any physician or doctor to intervene, and can also be used by a wide range of community as an objective screening methodology. The invented image processing procedure has been coded using MatLab language, and can be extended to open source freeware.

Most of the earlier pathological/biochemical techniques to address the problem of dementia diagnosis, actually use biopolymer markers, protein markers, amyloid deposits and peptides. These procedures are invasive, and need cellular materials from the patient, and are, hence, not commonly feasible. Therefore the latter methodology, being invasive, does not satisfy our requirement of being a harmless non-invasive technique. On the other hand, in the radiological diagnosis field, there are morphometric or volumetric imaging techniques to correlate with dementia, but these procedures need long time-consuming manual intervention by neuro-radiologists (who are much cost-intensive and not usually readily obtainable), and these procedures suffer from human visual subjective errors, the accuracy being around 75-90%. Furthermore, other exploratory neuroimaging procedures that use automated image processing approach to diagnose Alzheimer's disease, have an accuracy up to only 85-89% (compared to our 99%), and rely on imaging every voxel of brain, with heavy computational processing (in parametric space of about 100,000 dimensional feature vectors, in comparison to our parametric space of 2 or 3 dimensional feature vectors). Further those exploratory neuroimaging procedures need repeated manual checking in misregistration and image thresholding. In other words, our technique is considerable superior to the existing state of art.

There are a number of drawbacks and limitations in the existing imaging techniques. Their accuracy is lower, and they are neither rapid, automatic nor technician-operable. It is not possible to get all these requirements in a single method already existing commercially. It has been mentioned that for classifying dementia from plain raw MR images, there is no published patent that corresponds to our technique that implements the requirements of being brisk, automatic, objective, and over accurate (99%), without being computationally intensive nor requiring manual processing or intervention from radiologists. There are patents, which can satisfy parts of these requirements, but not the whole.

For instance, some procedures involve time-consuming morphometry by radiologists, while others are visually subjective or need point-by-point plotting of cortical deformation/thickness with heavy computer processing being involved (in a space of about 100,000 dimensions); indeed some of the processes known uses repeated manual checking in misregistration and image thresholding. These existing procedures have accuracy between 76-89%. All these techniques have utilized patient data sets below 100 individuals, whereas the development of our technique has involved much more individuals, around 200 subjects. Thus there is no patent satisfying all the wide-ranging requirements satisfied by the proposed invention.

To get a fundamental index of the cognitive dementic brain, inventors have symbiotically devised the method based on two powerful concepts:

(i) The Biological concept of the "Ventricualr zone", from which the cortex develops and which is the only region in the adult human brain that produces distant cortical neurogenesis.
(ii) The Mathematical concept of the "Topological dimensionality" which is a compact rigorous characterization of any space or contour that has a natural grainy irregularity in its disposition.

Inventors have selected the ventricular zone because different dementic diseases has different signatures on this ventricular zone which can be contoured in a single-projection single-slice MRI scan. Thereby, the topological dimensionality of the ventricular zone contour would be a very economical (and hence computationally readily measurable) index that would be a characteristic signature of the dementic process.

From a neurobiological viewpoint, the topological pattern of the ventricular zone (the original neural germinal tissue) is actually the generative template behind the development cerebral cortex and its distortion. Inventors topological dimension-computing algorithm is simple to operate and they have automated it. They have tested the feasibility of normalizability of the image processing operation by taking care to use image samples from all the regions of India with different ethnic groups: Northern, Southern, Eastern and Western zones. Inventors classification procedure in motivated by the principle of machine learning algorithm and artificial intelligence, which have earlier shown considerable ability to distinguish and classify biological signals in other contexts. Furthermore, inventors have taken much care and efforts to develop the technique using imaging inputs from scanners of different companies, and utilizing a large sample of over 200 patients, so that errors become much less and the statistical power of the analysis becomes much high.

However, among the methods available, it is known that imaging methods give more accuracy in dementia classification that methods using biochemical biomarker tests of body materials. There are a few patents on dementia classification using imaging analysis or biomarker analysis, such as Rubenstein et al., 1999 (U.S. Pat. No. 6,264,625), Rosse, et al, 1999 (U.S. Pat. No. 5,956,125), Shimura, et al., 2003 (U.S. Pat. No. 6,654,695), Scinto and Daffner, 2000 (U.S. Pat. No. 6,024,709), Kluger et al. (U.S. Pat. No. 6,067,986), Jackowski and Marshall (U.S. Pat. No. 7,074,576), Takahashi et al (U.S. Pat. No. 7,070,945). Nevertheless, these patents do not have as much accuracy as our proposed technique; moreover the existing procedures do not deal with any ready automated technique of image classification of dementic patients (which is the topic of the invention).

OBJECTS OF INVENTION

The main object of this invention is to develop a ready automated method for screening and diagnosis of Alzheimer's disease, even in an epidemiological or community based settings.

Other object is to differentiate Alzheimer's dementia from Mild cognitive deficit and from normal subjects.

Another object is to discriminate the different stages of Alzheimer's dementia like prodomal, mild or moderate.

Yet another object is to furnish ready automated diagnosis with over 99% accuracy.

Further object is to provide Radiological surrogate test of cognitive status, wherein MRI scanning image is processed to provide an objective cognitive instrument for estimating quantitatively the psychological ability of individuals (high correlation, P=0.97%).

STATEMENT OF INVENTION

This invention relates to a ready automated screening, diagnosis and classification technique for Alzheimer's disease using magnetic resonance imaging signal from ventricular zone contour of brain, wherein to get a fundamental index of the cognitive dementic brain the method utilizes. The biological concept of the 'ventricular zone' from which cortex develops and which is the only region in the adult human brain that produces distant cortical neurogenesis. The mathematical concept of the Topological dimensionality, which is a compact rigorous characterization of any space or contour that has a natural grainy irregularity in its disposition. We apply contour edge-detecting algorithm to the gray scale MRI image of the brain slice so as to produce a binary image of the contour of the ventricular zone. Employing the grid covering method (box counting algorithm) to calculate the first order topological metric index of the contour of ventricular zone. For developing the binary contour-image to be analyzed is superimposed on a succession of square grids of increasing edge length wherein the metric grid square is counted only once if the square is encountered by the border. Plotting the log of the number of metric grid squares encountered against the log of the edge length of the grid square, wherein the gradient of the plot is the linear topological metric index.

BRIEF DESCRIPTION OF ACCOMPANYING DRAWING

FIG. 1. shows the MRI image of the supra-callosal region of the brain showing the Ventricular zone contour whose signal is used for the procedure.

Figure 2:
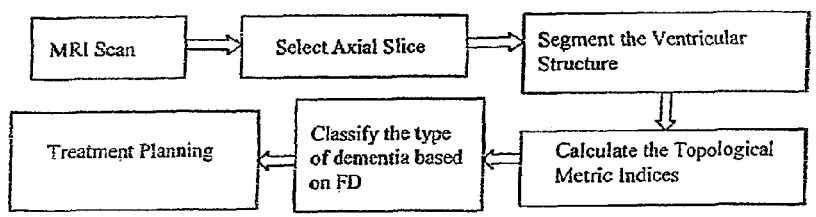

FIG. 2. illustrates flow diagram for the procedure of classification of dementia.

Figure 3:
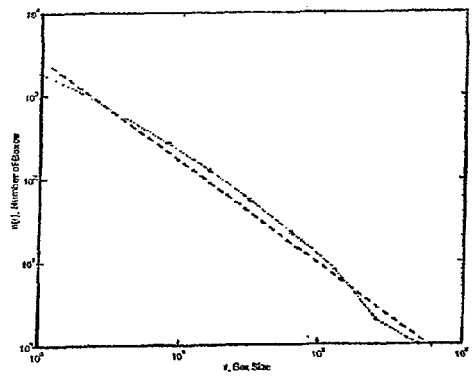

FIG. 3. shows the log-log plot whose gradient furnishes the first-order topological metric.

Figure 4:
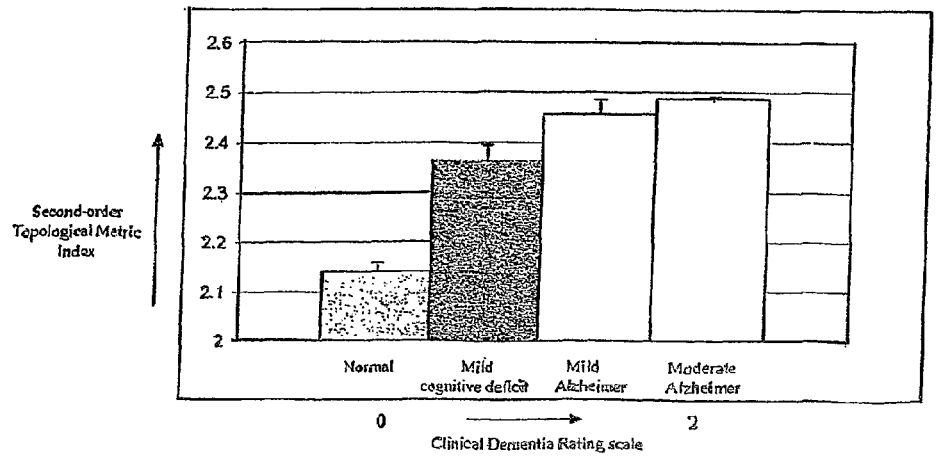

FIG. 4. demonstrates classification of dementia by second-order topological metric index using 1-D parameter space. Note that as the Dementia grading increases, the second-order index increases. Any overlap is further lessened by increasing a feature vector and mapping in 2-D space as in FIG. 5.

Figure 5:
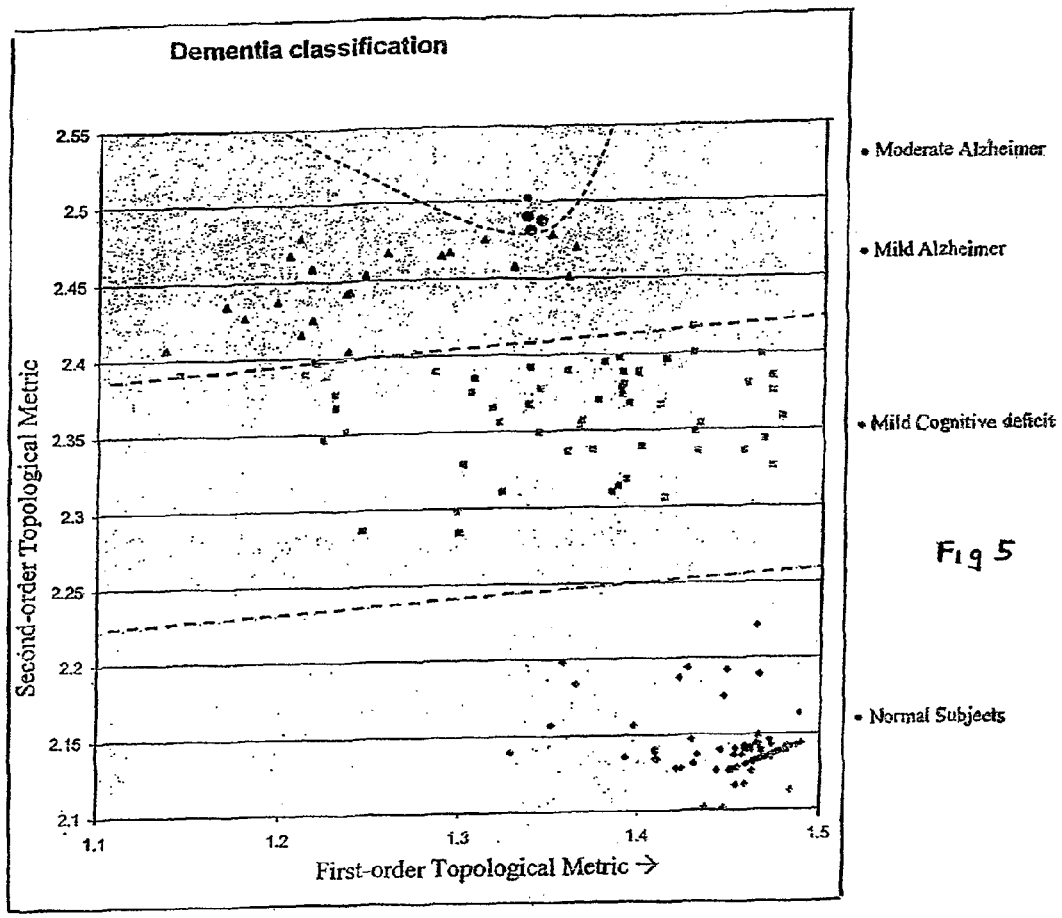

FIG. 5. shows nonlinear Automated Classifier in 2-D parametric space so as to distinguish between Normal and Dementic subjects (100% accuracy), between Normals and Mild cognitive deficit (100% accuracy), and between Mild Cognitive deficit and Mild Alzheimer's disease (99.5% accuracy). Each point plot is of a single individual, there are total 200 individuals. Many of the normal individuals are tightly clustered in the lower right region and the individual points may not be separately visible. The four groups of patients (four patient-clusters) can be further separated in a third dimension by using another extra dimension feature vector (a higher-order or third-order index) so that the patient points are mapped in a higher space of 3 parametric dimensions (FIG. 6).

Figure 6:
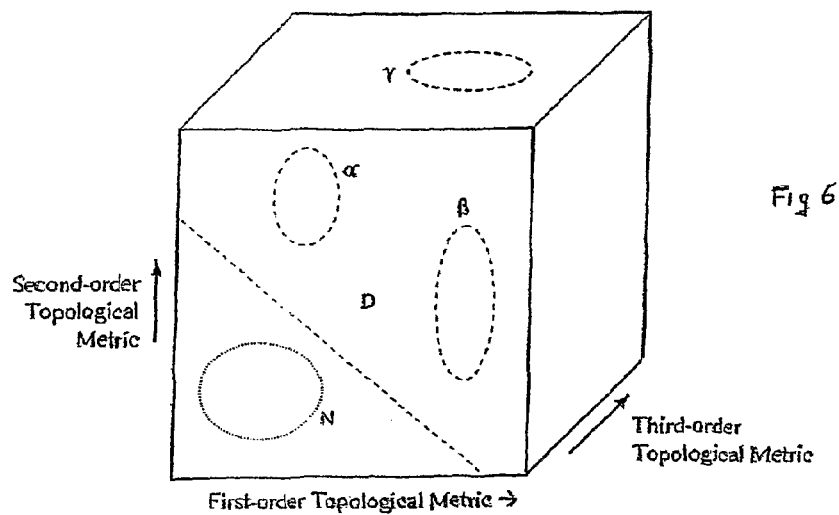

FIG. 6. illustrates linear automated classifier schemata using 3-D parameter space of three feature vectors (first, second and third-order topological metric indices) to increase discrimination between Normal subject region N and Dementic subjects region D which consists of the sub-zones Mild Cognitive deficit α Mild Alzheimer disease β and Moderate Alzheimer's disease γ. Increasing the number of feature vectors increases the discrimination power. There is 100% accuracy of the automated classifier in distinguishing between Normal and Dementic subjects, while the accuracy is 99.5% in distinguishing between Mild cognitive deficit and Mild Alzheimer's disease.

DETAILED DESCRIPTION OF INVENTION

The suggested non-invasive technique is able to classify Alzheimer dementia staging on analyzing plain structural magnetic resonance images ($T_1$ weighted MRI), without much involved manual time-consuming processing stages. The present procedure used the MRI signal from the contoured ventricular zone, which is the neurogenesis zone of the adult human brain and is critically affected by various neurodegenerative diseases and their stages differentially. Inventors develop a topologically-based technique by using a dynamic grid method to fine the pattern of incongruity vis-à-vis the contoured ventricular zone of normal brain. The technique can improve the early detection of dementia, with over 99.5% accuracy, by developing a screening test that can be done automatically (without needing the expensive and scarce input of neurologists or radiologists).

The proposed technique is applicable for the classification of dementia as well for the differentiation of the stages of dementia, such as between Normal individuals and those with Mild Cognitive deficit. Mild Alzheimer's disease, and Moderate Alzheimer's disease. It is known that the only effective management of such neurodegenerative disease is to diagnose it at the early mild stage, when the progress of the disease can be effectively slow down by proper intervention, and recently disease-modifying agents are under trial in various centers that may considerably decelerate the advancement of the disease process, if the prophylactic treatment are instituted in the earliest stages. Under this perspective, our proposed technique may be useful for:
 (i) Timely initiation of preventive or therapeutic interventions in the mild stage of the disease.
 (ii) Monitoring the progress of the dementia process,
 (iii) Estimating the therapeutic efficiency of treatment interventions.

The proposal reports for the first time the proof-of-principle of a technique based on metric topology-based principle of processing of magnetic resonance imaging, whereby the technique has considerable potentiality to be used for the early detection of dementia. Ever since the initiation of digital imaging technology, image-processing techniques have been dominated by spatial and frequency filters based techniques. Nevertheless, as the work in the laboratory shows, the proposed novel neuroimaging procedure as metric topology-based imaging, founded firmly on biologically-oriented properties of subventricular region of brain, furnishes information can be used strategically for improving the efficiency of pre-clinical dementia diagnostic and therapeutic programs.

Dementia due to neurodegenerative condition, is one of the most common disorders among the elderly; it causes a progressive decline in cognitive functions such as memory, attention and language. Dementia due to Alzheimer's disease and Mild cognitive deficit constitute a foremost common disorder past the middle age. For dementia diagnostic analysis of radiological images of the brain, it was needed to choose a specific region of the brain, which should satisfy the following properties"

The region should be easily rapidly and automatically selected and segmented fast by a computer (hence the data set of the region should be compact and not be large like the whole cortex and should not need manual/radiologist intervention nor morphometry).

The region should be a zone where the various dementic diseases have their characteristically different alteration of the structure and pattern of the tissue;

The region should be a basic template that should be genetically, cytologically and developmentally linked directly to the formative radial brain architecture and its elastoplastic distortion in dementia.

The brain region that satisfies these characteristics is the ventricular zone, whose contour can be easily demarcated in a computer using a rapidly acquired plain MRI single-scale $T_1$, scan at axial plane, across the supra-callosal level of the brain (FIG. 1). A major significant fact is that the ventricular zone is the only region in the adult human brain that has active neuronal proliferation or neurogenesis that links to distant cerebral regions and this neurogenesis is modulated differentially by different neurodegenerative diseases: down-regualted in Alzheimer's dementia while upregulated in Parkinson's dementia. Quantitatively, the contours of biological objects can be most rigorously and accurately be characterized by the mathematical concept of topological metric, namely the fractiled index, which is indeed referred to the fundamental fractured patterning of nature, measuring the irregular grainy texture of biological objects. Further, it is well known histologically that as Alzheimer's diseases progresses the irregularity of the ventricular contours increases.

The first topologically fractiled object to be studied has been the natural kinetic motion of biological objects as microorganisms and pollen grain (Brownian motion), whose quantitative investigations were carried out by Einstein, Fokker and Planck. Later the concept of topological irregularity was generalized to the exploration of fractiled patterning in biological or human systems, by Hilbert and Courant, and by the Indian statisticians Mahalanobis and Rao. Motivated by these approaches, the P.I initially probed the use of fractiled topological texture to diagnose microscopic imaging inputs at Indian Statistical Institute from a clinical pathology perspective. Later at NRBC inventors have developed the topological metric pattern analysis approach for a practical neuroimaging application to the diagnosis of neurodegenerative disease (FIG. 2).

Topological dynamics and fractured geometry has proven to be very useful tool in quantifying the structure, function and abnormally of a wide range of biological systems, as cardiovascular, pulmonary and immunological systems, with application respectively to early diagnosis of cardiac failure, obstructive pulmonary disease and malignant transformation. Actually, it has been found that as a disease advances, its progressive intensity of morbidity is reflected in the alternation of the fractiled index of the relevant signal (e.g. there is increase in the said index of R-R plot from cardiac ECG signal, as the stage of cardiac decompensation rises). A fractiled system has a property that more fine structure is revealed as the object is magnified, similarly the concept of morphological complexity implies that more fine structure (increased resolution and detail) is revealed with increasing magnificent. The topological metric index as fractiled index measures the rate of addition of structural detail with increasing magnificent, scale or resolution. There are several approaches to measuring topological metric indices of an outlined contoured object, e.g:
(i) First-order metric as length-scaling methods, providing linear fractiled index.
(ii) Second-order metric as area-scaling methods, furnishing planar fractiled index.

For instance to obtain the first-order metric index, inventors proceed as follows. A gray scale MRI image of the brain slice, is taken and we apply first a contour edge-detecting algorithm to the image so as to produce a binary image of the contour of the ventricular zone. Then they employ the grid covering method (box counting algorithm) to calculate the first-order topological metric index of the contour of the ventricular zone. The flowchart for the implementation of this algorithm is shown in FIG. 2, where they use the grid metric method to compute the topological index. The grid metric method is based on the concept of serially enveloping the contour. For enveloping, the binary contour-image to be analyzed is superimposed on a succession of square grids of increasing edge lengths. A metric grid square is counted only once if the square is encountered by the border, irrespective of the number of pixels that encounter the square. Then, the log of the number of metric grid squares encountered is plotted against the log of the edge length of the grid square. For any binary contour of the ventricle of MRI image of the brain, the log-log plot of the number of grid squares versus the length of the square's edge, gives a linear relationship as shown below in FIG. 3. The gradient of the plot, as obtained by the method of best fit, is the linear topological metric index, etc, by altering the methodology of covering the region in question by an envelope.

On the other hand, the second-order metric is obtained from the gradient of the log-log plot between of the number of boxes covering the contour vis-à-vis the number of boxes encompassing the area, using a grid enumeration algorithm. Actually, the entire procedure of determining the said two topological indices of the ventricular zone contour of the brain comprises two major steps which are done automatically: (i) counting the number of squares needed to envelop the region of the ventricular zone, and (ii) performing the single gradient analysis (least-squares fit) to obtain the precision topological indices.

To enable these automatic processing to take place, the technician normalizes the brain image using automated SPM5 freeware with MatLab software, selects the axial slice of the MRI volume image, and crops the ventricular region (i.e. Region of Interest, ROI). The origin of the metric grid is chosen randomly in the images for removing any positional bias in the performance of the counting of grid squares. Inventors develop a computationally efficient algorithm in estimate the topological metric index of the ventricular zone contour.

Inventors consider the second-order index as a possible index as a possible classifying feature vector. The representative second-order index of various clinical groups such as Normal or non-dementia group (N), Mild Cognitive deficit (MiC), Mild Alzheimer (MiA) and Moderate Alzheimer (MoA) groups are respectively 2.16, 2.38, 2.45 and 2.50, while the respective standard deviation of the groups are small, being correspondingly ±0.069, ±0.043, ±0.024, and ±0.005. These data for the classification by second-order index of the individual into the four groups are shown in FIG. 4. There is almost complete separation between the four groups, but still there is a small overlap (about 2% superimposition, with accuracy of classification=98%). To decrease the overlap and increase the accuracy, we take another feature vector, say the first-order index.

The clinical groups show definitive clusters in the 2-D feature space of the first and second order indices (FIG. 5). There are clear linear (curvilinear discrimination) separating the clinical groups without any overlap. Inventors develop an automated classification algorithm by machine learning using proper radial basis functions (RBF) kernel.

The validation of the above soft computing-based classification approach has been performed on a large dataset of MRI scans of about 200 individuals (patients and normal subjects) randomly allotted as Training Sets and Testing Sets, in the ratio of 2:1. For the Training Set, for each individual we know his/her Clinical Dementia Rating (CDR) score as also the 4-stage diagnosis, namely Normal, MiC, MiA and MoA classification algorithm using the 2-D space, based on the cross-validation accuracy of the training set. To test the predictive accuracy of the methodology, the classification algorithm is then evaluated on an unseen said Test Set, we classify the image and predict its 4-stage diagnosis (N, MiC, MiA, MoA). The automated classification is then matched with the actual diagnosis of the individual and his/her clinical dementia rating score (N, MiC, MiA, MoA). The accuracy of the classifier can be still further increased by using more features vectors, such as higher topological metrics, such first-order, second-order and third-order indices, which map the dementic process of the brain in 3-D feature space (FIG. 6).

It may be mentioned that the correlation coefficient between the second-order topological metric index of the image and the patient's cognitive score index (Washington CDS score) is almost perfect, being as high as 0.097. This gives a firm foundation of our proposed approach of "Radiological cognitive testing" whereby the cognitive status of a patient can be estimated by an objective radiological method using topological from the MRI image, vis-à-vis the actual stage diagnosis of the patient is excellent. There is no misclassification between the Normal subject group vis-à-vis the Mild cognitive deficit group (classification accuracy=100%), while there is only 1 misclassification between the Mild cognitive deficit group vis-à-vis the Mild Alzheimer group (classification accuracy=99.5%). Furthermore, the said methodology can distinguish normal (control) subjects vis-à-vis dementia patients at an accuracy of 100% in our trails. Needless to say, this accuracy is the highest among all the automated methods of MRI processing techniques available till date.

The invented technique can be used for:
Ready Objectively Screening (ROS) of patients of mild cognitive deficit and early Alzheimer's disease, from normal population, in a community-based setting or in a clinic-based milieu.
Distinguishing Mild cognitive deficit from early Mild Alzheimer's disease, both in a community based setting and in clinics.
Demarcating Mild Alzheimer's disease from Moderate Alzheimer's disease in the populace.
Diagnosis of the different stages of Alzheimer's dementia.
Generalized application to scans from any manufacturer of the MRI electrical/electrical & electronics industry.
Furnishing brisk automated differential diagnosis with 100% accuracy between normal and mild cognitive deficits, and with 99.5% accuracy between mild cognitive deficits and mild Alzheimer's disease.
Fullest concordance of the Topological metric of the invented algorithm, with cognitive testing as Clinical Dementia Rating index (CDR).
Radiological Cognitive Testing: Using an MRI scanning device as an objective cognitive instrument to quantitatively estimate the psychological ability of individuals, particularly when psychometric experts are unavailable, or when the subject is uncooperative or unable to take a psychometric test.

We claim:

1. A method for ready automated screening, diagnosis and classification of Alzheimer's disease using magnetic resonance imaging (MRI) signal from ventricular zone contour of brain, wherein to get a topological index of the cognitive dementic brain the method comprises of the following steps:
   i) obtaining a gray scale MRI image of a brain slice,
   ii) applying a contour edge-detecting algorithm to the image to produce a binary image of the contour of the ventricular zone,
   iii) employing a grid covering method to calculate the first order topological metric index of the contour of ventricular zone,
   iv) superimposing the binary contour image on a succession of square grids of increasing edge length wherein a metric grid square is counted only once if the square is encountered by a border of the binary contour image; and
   v) plotting the log of the number of grid squares encountered against the log of the edge length of the grid area, wherein the gradient of the plot is the linear topological metric index.

2. The method as claimed in claim 1, wherein using imaging data from MRI scanners of different companies and utilizing large sample over 200 patients; the error become much less and the statistical power of the analysis becomes much higher.

3. The method as claimed in claim 1, wherein a topologically based technique by using a dynamic grid method to find the pattern of incongruity vis-a-vis the contoured ventricular zone of brain.

4. The method as claimed in claim 1, wherein the novel neuroimaging procedure as metric topology based imaging, founded firmly on biologically-oriented properties of sub-ventricular region of brain can be used strategically for improving the efficiency of preclinical dementia diagnostic and therapeutic programs.

5. The method as claimed in claim 1, wherein a specific region of the brain is chosen, where various dementic diseases have their characteristically different alteration of the structure and pattern of the tissue.

6. The method as claimed in claim 1, wherein the specific region of the brain should be a basic template that should be genetically, cytologically and developmentally linked directly to the formative radial brain architecture and its elastoplastic distortion in dementia.

7. The method as claimed in claim 1, wherein the chosen brain region is demarcated using a rapidly acquired plain MRI single-scale T, scan at axial plane, across the supra-callosal level of the brain.

8. The method as claimed in claim 1, wherein the contours of biological objects can be accurately characterized by the mathematical concept of topological metric namely the fractiled index, measuring the irregular grainy texture of biological objects.

9. The method as claimed in claim 1, wherein the topological metric index as fractiled index measures the rate of addition of structural detail with increasing magnificent, scale or resolution.

10. The method as claimed in claim 1, wherein the method is used as ready objective automated screening of patients of mild cognitive deficit and early Alzheimer's disease, from cognitively normal population, in a community-based setting or in a clinic-based milieu.

11. The method as claimed in claim 1, wherein the method is used in distinguishing Mild cognitive deficit form early Mild Alzheimer's disease, both in a community based setting and in clinics.

12. The method as claimed in claim 1, wherein the method is used in demarcating Mild Alzheimer's disease from Moderate Alzheimer's disease patients in the populace.

13. The method as claimed in claim 1, wherein the method is used in diagnosis of the different stages of Alzheimer's dementia (AD) such as Moderate AD and Severe AD.

14. The method as claimed in claim 1, wherein the method is used in furnishing brisk automated differential diagnosis with 100% accuracy between cognitively normal individuals and mild cognitive deficit individuals, and with 99.5% accuracy between mild cognitive deficit individuals and individuals with mild Alzheimer's disease.

15. The method as claimed in claim 1, wherein the method is used in determining the cognitive functional level of individuals, as Clinical Dementia Rating index (CDR).

16. The method as claimed in claim 1, wherein the method is used for Radiological Cognitive Testing and Imaging Biomarker, and wherein an MRI scanning device is used as an objective instrument to quantitatively estimate the cognitive impairment and psychological ability of individuals.

* * * * *

UNITED STATES PATENT AND TRADEMARK OFFICE
CERTIFICATE OF CORRECTION

PATENT NO. : 8,577,106 B2  Page 1 of 1
APPLICATION NO. : 13/133038
DATED : November 5, 2013
INVENTOR(S) : Roy et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 252 days.

Signed and Sealed this
Twenty-second Day of September, 2015

Michelle K. Lee
*Director of the United States Patent and Trademark Office*